United States Patent [19]

Outtrup

[11] 3,979,261

[45] Sept. 7, 1976

[54] PRODUCTION OF GLUCOSE ISOMERASE BY BACILLUS COAGULANS

[75] Inventor: Helle Outtrup, Vaerloese, Denmark

[73] Assignee: Novo Industri A/S, Bagsvaerd, Denmark

[22] Filed: Dec. 27, 1973

[21] Appl. No.: 428,682

[30] Foreign Application Priority Data

Jan. 12, 1973  United Kingdom............... 1773/73

[52] U.S. Cl. ............................... 195/65; 195/31 F
[51] Int. Cl.$^2$ ....................................... C12D 13/10
[58] Field of Search ............... 195/65, 66 R, 31 F

[56] References Cited
UNITED STATES PATENTS

| | | | |
|---|---|---|---|
| 3,826,714 | 7/1974 | Suekane et al. | 195/31 F |
| 3,847,740 | 11/1974 | Heady et al. | 195/31 F |
| 3,847,741 | 12/1974 | Heady et al. | 195/31 F |

FOREIGN PATENTS OR APPLICATIONS 46-36192  10/1971  Japan

OTHER PUBLICATIONS

Danno, Agr. Biol. Chem. vol. 34, No. 12, pp. 1795–1804; 805–814, (1970).
Chemical Abstracts vol. 76, 32898j (1972).
Yoshimura et al. Agr. Biol. Chem. 30, 1015–1023. (1966).

*Primary Examiner*—Lionel M. Shapiro

[57] ABSTRACT

A superior glucose isomerase is present intracellularly in an atypical *B. coagulans* characterized by an ability to grow on inorganic sources of nitrogen.

2 Claims, No Drawings

PRODUCTION OF GLUCOSE ISOMERASE BY BACILLUS COAGULANS

The invention relates to glucose isomerase, to methods for the production of this enzyme and to enzymatic isomerization of glucose to fructose with glucose isomerase.

Syrups containing a mixture of glucose and fructose are widely used in industry because of their sweet taste and their low tendency to crystallize. Such syrups are preferably produced from glucose syrups using an enzyme to catalyze the isomerization of glucose to fructose. It is important for the economy of this process that the enzyme costs are low and that there be a negligible formation of by-products, which will have to be removed before the syrup can be used.

Enzymes capable of isomerizing glucose to fructose may be obtained from a large number of different microorganism species, and the properties of the enzymes vary from species to species. Enzyme properties, which are particularly important for the use in the isomerization process are, stability at high temperatures and activity at low pH values.

In an enzymatic isomerization of glucose to fructose, the following conditions are of importance:

pH: A pH value as low as possible is desired in order to avoid the alkali-catalyzed by-product formation, i.e. below pH 7, pH 5–7 is a suitable range.

Temperature: The enzyme should be stable at a temperature of about 55°C to 75°C, which is the usual reaction temperature.

Solubility: In many cases it is desired to use the microorganism cells containing the enzyme intracellularly for the isomerization; it is therefore very important that as little as possible of the enzyme leaks out in the reaction mixture during isomerization or during handling of the cells after isomerization. It is furthermore of importance in the production of the enzyme preparation that the cells easily may be dried in such a way that the enzyme will not leak out of the cells.

In other methods soluble enzyme is desired. This may be used either directly, or it may be made insoluble by coupling to an insoluble carrier. For this process it is important that the enzyme can be easily extracted from the cells.

As the price margin between glucose and isomerized glucose is very small, it is furthermore extremely important that the production yield of the enzyme is high, so that the price of the enzyme preparation can be sufficiently low.

It has now been found that by using the isolation method according to this invention, it will be possible reproducibly and with high frequency to isolate organisms from nature, which will be able to produce a glucose isomerase, which has extremely good heat stability and a very low pH optimum.

The organisms isolated in this way are aerobic spore-forming rod-shaped bacteria. They must be classified as a thermophilic Bacillus species, and more specifically are identifiable as an atypical *B. coagulans*, differentiated from typical *B. coagulans* strains by an ability to grow at 65° C and to grow on inorganic sources of nitrogen.

The isolation method according to the invention consists in incubating sources of microorganisms, e.g. soil samples, on media containing only ammonia as nitrogen source, xylose as carbon source and the usual trace elements as inorganic salts. The incubation must take place at a temperature above 60°C, preferably between 60° and 65°C, to ensure growth only of thermophilic microorganisms. Agar in a concentration of 1.5–3% may be added to the medium in order to make the isolation of the developing organisms simpler. The organisms developing on this medium are purified by plating on agar medium of the composition described above and at the same temperature. The pure cultures thus obtained are then tested for glucose isomerase activity using a simple semi-quantitative test, e.g. as described below in Example 1, the cultures giving a positive reaction are selected.

The rationale of the entire isolation technique is to establish growth conditions which will encourage rapid growth of microorganisms most adapted to industrial utilization and likely to produce a glucose isomerase.

Incubation at elevated temperatures, e.g. 60°C, encourages growth of thermophilic microorganisms. As a class, thermophiles have the high growth rates desired for industrial fermentation processes. In addition, the enzymes produced by thermophiles are thermostable.

Xylose is the carbon source since all known glucose isomerases are basically xylose isomerases. Many organisms which digest xylose will contain a glucose isomerase. The screening therefore is an effort to locate organisms which can use xylose as their sole source of carbon.

Ammonia, i.e. an inorganic nitrogen source, is employed to exclude microorganisms that require organic nitrogen including notably *B. coagulans*, a microorganism species that would otherwise fit all the conditions of the screening program. Actually, *B. coagulans* is a known source of a quality glucose isomerase, one with relatively good heat stability and a low pH optimum for both activity and stability. Unfortunately, *B. coagulans* is expensive to cultivate because its growth requirements include vitamins, and amino acids.

The microorganisms isolated by the above described screening procedure have a number of properties in common and, it is believed, are classifiable in a single species. However, the species in question would seem to be that of *B. coagulans*. An apparent identity between *B. coagulans* and the microorganisms of the present invention is not surprising since the screening conditions are so very close to conditions which would select *B. coagulans* that obtaining closely related microorganisms should be expected. In addition, *B. coagulans* is a poorly defined species with several subgroups already known to exist. The literature on *B. coagulans* acknowledges that a vigorous investigation of *B. coagulans* is likely to establish that *B. coagulans* constitutes several different species of related microorganisms. Pending a definitive investigation of *B. coagulans*, all that can be said of the microorganism of the present invention is that it is an atypical *B. coagulans* characterized in its atypicality by being capable of capable of growth on inorganic sources of nitrogen.

A biochemical distinction of importance to the present invention is that the glucose isomerase enzyme of the atypical *B. coagulans* does differ from the glucose isomerase of (typical) *B. coagulans*, notably with regard to thermal stability and the effect of pH and temperature on activity. The glucose isomerase of the present invention is more thermostable and its activity at pH 6 to 7 is as good, if not better. In total a different enzyme is present.

For production of the glucose isomerase of the present invention, the bacteria are cultivated aerobically on media containing usual salts and sources of carbon and nitrogen at a pH between pH 5 and pH 9. Addition of xylose or xylose containing compounds to the medium is necessary in order to induce glucose isomerase formation in the wild strains. It is however possible to isolate mutants which produce glucose isomerase without induction by xylose. When such microorganisms are cultivated, any metabolizable carbon source may be used.

Incubation temperature for the fermentation is between 40° and 65°C, usually around 50°C. Aerobic conditions are maintained during the cultivation by blowing air through the medium, e.g. at a rate of approximately one volume of air per volume of liquid per minute.

The enzyme is formed intracellularly and the purification procedure usually consists in harvesting the cells by centrifugation or filtration and if desired drying of the cell cream by lyophilization, spray drying or by any other process which will not destroy the enzyme activity. Before drying, the cells may be treated with solutions of Cobalt salts, so that the enzyme preparation will contain an amount of $Co^{++}$ necessary to activate the enzyme.

The harvested cells may furthermore be heat-treated at a temperature between approximately 70°–80°c for a time sufficient to destroy the lytic enzyme systems within the cells.

During cultivation, the amount of glucose isomerase present in the cells may be measured at intervals by determining the amount of fructose formed from glucose under standard conditions. When there is no more increase in activity, the cells are harvested.

If a soluble enzyme product is desired, it will be possible to conduct the fermentation so that most of the enzyme leaks out of the cells into the fermentation broth. This can for instance be done by raising the fermentation temperature to 60°C during the whole fermentation period or only during the latter part of it.

An enzyme preparation may be prepared from this broth using the usual methods for the preparation of extracellular enzymes, i.e. purifying the broth by centrifugation or filtration and concentrating the enzyme containing solution by evaporation or reverse osmosis, thus obtaining a liquid enzyme product, or by precipitating the enzyme out of the broth or the concentrated broth by means of salts or water soluble solvents and finally drying the precipitate.

A soluble enzyme may also be prepared from the isolated cells by letting them autolyze, by addition of lytic enzymes, e.g. lysozyme or by the addition of surface active agents, furthermore by mechanical rupture of the cells such as by ultra-sonics or by the use of mechanical homogenizing devices. Enzyme preparations can be prepared from cells treated in this way by the methods described above.

Normally the microorganisms will produce a number of spores during the fermentation. If a spore-free preparation is desired, an asporogenic mutant should be used for the cultivation. Methods for the isolation of asporogenic mutants are well known in the art and it is easy to isolate this type of mutants.

If desired, the enzyme preparation according to the invention may be imbedded into a matrix or insolubilized by any method known in the art which will not destroy the enzyme activity.

The present enzyme has properties which are very favorable for glucose isomerization under the favorable commercial conditions of pH 5–7. It may be used from 55°–85°C without substantial loss of activity down to pH values at about 5. It is extremely heat stable, retaining much of its activity at 85°C over the entire pH 5 to pH 7 range. By contrast, the activity of known *B. coagulans* glucose isomerase loses activity with temperatures in excess of 70°C, having almost no activity at 85°C. Superiority in properties of the enzyme make all the more advantageous the economies achieved by cultivating the microorganism on inorganic nitrogen.

For further understanding of this invention, the following specific examples thereof are presented.

EXAMPLE I

Isolation of glucose isomerizing organisms from nature

A 10% suspension of garden soil in sterile water was spread on plates which contained an agar medium of the following composition in g per liter of distilled water:

| | |
|---|---|
| $(NH_4)_2SO_4$ | 3 |
| $K_2HPO_4$ | 1 |
| $MgSO_4, 7H_2O$ | 0.5 |
| KCl | 0.5 |
| $FeSO_4$ | 0.01 |
| agar | 20 |
| xylose | 5 | was autoclaved separately and added aseptically just before pouring the plates.

The plates were incubated at 60°–65°C for 2 days and the colonies which developed were transferred to a medium of the following composition in g per liter of distilled water:

| | |
|---|---|
| peptone | 10 |
| tryptone | 5 |
| yeast extract | 3 |
| $Na_2HPO_4, 12H_2O$ | 18 |
| $MgSO_4, 7H_2O$ | 0.2 |
| $KH_2PO_4$ | 7 |
| agar | 20 |
| xylose | 10–20 | was autoclaved separately and added aseptically just before pouring the plates.

If the culture appeared to be impure, it was restreaked on the first medium and again transferred to the rich medium. This procedure was repeated until a pure culture was obtained.

The cultures on the rich medium were incubated for 1–2 days at 60°C and were then tested for the ability to isomerize glucose to fructose in the following manner:

The cells were suspended in 0.9% NaCl. One (1) ml of cell suspension was incubated at 70°C with 1 ml of the following solution:

| | | |
|---|---|---|
| glucose | 80 | grams per liter |
| TRIS | 0.1 | mole per liter |
| chloroform | 2 | ml |
| $MgSO_4, 7H_2O$ | 5 | grams per liter |
| $CoCl_2, 6H_2O$ | 0.5 | grams per liter |
| pH was adjusted to 6.5 using HCl. | | |

After 4 hours of incubation, one droplet of the reaction mixture was transferred to a sheet of chromatographic paper (Whatman No. 1) by means of a Pasteur pipette. The droplets were arranged in a manner allowing space for 50–100 droplets per sheet of paper. After drying, the paper was moistened in the following solution:

| | |
|---|---|
| naphtalindiol 1,3 | 250 mg |
| ethanol | 250 ml |
| ConcHCl | 20 ml |

After drying for at least 30 minutes at room temperature the paper was heated at 60°c for 1–20 minutes. If the reaction mixture contained at least 0.5% fructose, a brown spot became visible after this treatment.

Eighteen cultures giving positive reactions for fructose using this method were isolated. The cultures are deposited at the Northern Regional Research Laboratory, Peoria, Ill., USA (NRRL) under the numbers NRRL B-5649 to NRRL B-5666.

These strains have the following properties in common:

Morphology:
Similar to that of the species in the *B. subtilis* group.

Biochemical reactions:
Temperature, for growth: 40°–65°C, optimum 55°–60°C. Growth inhibited by high concentrations of protein (above 3%) and carbohydrates (1%). Acid is produced from glucose, xylose, fructose, ribose and glucerol (no gas formed); arabinose is not fermented.

No growth in 3 % NaCl.

Growth at pH 5.7: positive.

Growth on glucose-nutrient agar better than growth on nutrient agar. Good growth on soybean agar.

Hydrolysis of casein and starch positive when tested at 40°C, weak or negative when tested after growth at 50°C.

Negative hydrolysis of gelatine.

Anaerobic growth in glucose medium, negative (weak).

EXAMPLE II

Production of glucose isomerase in shake flasks

In baffled 500 ml Erlenmeyer flasks was prepared 100 ml of a medium with the following composition (in grams per liter tap water):

| | |
|---|---|
| corn steep liquor | 80 |
| yeast extract | 5 |
| $K_2HPO_4$ | 1 |
| $(NH_4)_2SO_4$ | 5 |
| xylose | 4 |
| $MgSO_4, 7H_2O$ | 0.2 |
| $MnSO_4, H_2O$ | 0.05 |

Xylose, $MgSO_4$ and $MnSO_4$ were autoclaved separately and were added aseptically after cooling to room temperature. pH was aseptically adjusted to 7.0 using sterilized 4N NaOH.

The flasks were inoculated with 1 ml of a suspension of cells in sterile distilled water prepared by scraping off growth from slants on the rich medium described in Example I.

The inoculated flasks were incubated on a rotary shaking table (220 rpm) at 50°C. After 40 hours of incubation, the contents of the flasks were centrifuged and the cells obtained in the precipitate were used for isomerization of glucose in the following way:

In a reactor provided with means for maintaining a constant temperature, nitrogen atmosphere, pH control and stirring was placed 0.5 liter of a 40% (w/w) solution of dextrose, $H_2O$ in distilled water to which was added 0.5 g of $MgSO_4, 7H_2O$ and 0.05 g of $CoSO_4, H_2O$.

Glucose isomerase containing cells from 1 liter of medium were added to the solution and the isomerization process took place under the following conditions: Temperature: 80°C; pH: 6.2; Time: 10 hours.

The amount of fructose formed was determined by polarimetry and the degree of isomerization was determined as % fructose formed/initial % of dextrose. The following results were obtained:

| Strain NRRL No. | % Conversion |
|---|---|
| 5649 | 35 |
| 5650 | 44 |
| 5651 | 42 |
| 5652 | 44 |
| 5653 | 47 |
| 5654 | 44 |
| 5655 | 50 |
| 5656 | 42 |
| 5657 | 42 |
| 5658 | 38 |
| 5659 | 38 |
| 5660 | 42 |
| 5661 | 42 |
| 5662 | 51 |
| 5663 | 42 |
| 5664 | 44 |
| 5665 | 42 |
| 5666 | 47 |

EXAMPLE III

Thermophilic Bacillus NRRL No. 5650 was cultivated overnight in nutrient broth at 48°C. One ml of this culture was transferred to a 500 ml baffled Erlenmeyer flask containing 100 ml of the following medium (in gram per liter distilled water):

| | |
|---|---|
| $Na_2HPO_4, 2H_2O$ | 9 |
| $KH_2PO_4$ | 7 |
| $MgSO_4, 7H_2O$ | 0.5 |
| KCl | 0.5 |
| $FeSO_4$ | 0.01 |
| antifoam | 0.1 |
| $(NH_4)_2SO_4$ | 3 |
| xylose | 5 | was autoclaved separately and added aseptically before inoculation.

The flask was incubated on a rotary shaking table at 48°C for 1–2 days. The glucose isomerizing activity was tested as described in Example II; the result was 32% conversion.

EXAMPLE IV

Isolation of mutant bacteria which are able to produce glucose isomerizing activity in xylose-free media Logarithmically growing cells in nutrient broth were harvested and suspended in TRIS-maleate buffer pH 6.0 containing 100 micrograms of N-methyl-N'-nitro-N-nitrosoguanidin per ml. The suspension was incubated at 37°C for 30 minutes, whereafter the cells were washed diluted and spread on petri dishes containing nutrient agar.

After 1-2 days at 50°-60°C, colonies of mutant strains were transferred to petri dishes containing a xylose-free medium of the following composition in gram per liter of distilled water:

| | |
|---|---|
| yeast extract | 30 |
| agar | 20 |

The plates were incubated until good growth was obtained (1-2 days). The glucose isomerase activity of the colonies was now determined using the simple method described in Example I.

The number of mutants found was high, about one in 2,000 to 3,000 colonies tested.

I claim:
1. A process for the production of glucose isomerase, comprising cultivating under aerobic conditions an atypical *Bacillus coagulans* productive of a glucose isomerase, said *Bacillus coagulans* being capable of growth on only inorganic nitrogen sources as the nitrogen source and at a temperature of 65°C on a nutrient medium containing a nitrogen source, a carbon source, optionally including xylose, small amounts of inorganic salts, at a pH value between 5 and 9 and a temperature between 40° and 65°C, whereafter the glucose isomerase thus produced is recovered.

2. A process as claimed in claim 1 in which a mutant atypical *Bacillus coagulans* strain is cultivated in a growth medium free of xylose.

* * * * *